(12) United States Patent
Grehan et al.

(10) Patent No.: US 11,839,891 B2
(45) Date of Patent: Dec. 12, 2023

(54) PROTECTION OF APERTURE PLATE DURING AEROSOL GENERATION

(71) Applicant: STAMFORD DEVICES LIMITED, Dangan (IE)

(72) Inventors: Joseph Grehan, Gort (IE); Noel Coyle, Craughwell (IE); Russell Greaney, Carnmore (IE); Stephen Thornton, Oughterard (IE)

(73) Assignee: Stamford Devices Limited, Galway (IE)

( * ) Notice: Subject to any disclaimer, the term of this patent is extended or adjusted under 35 U.S.C. 154(b) by 566 days.

(21) Appl. No.: 16/621,604

(22) PCT Filed: Aug. 23, 2018

(86) PCT No.: PCT/EP2018/072824
§ 371 (c)(1),
(2) Date: Dec. 11, 2019

(87) PCT Pub. No.: WO2019/038408
PCT Pub. Date: Feb. 28, 2019

(65) Prior Publication Data
US 2020/0156098 A1 May 21, 2020

(30) Foreign Application Priority Data
Aug. 25, 2017 (EP) .................................. 17188034

(51) Int. Cl.
*B05B 12/08* (2006.01)
*A61M 11/00* (2006.01)
(Continued)

(52) U.S. Cl.
CPC ......... *B05B 12/081* (2013.01); *A61M 11/005* (2013.01); *A61M 15/0085* (2013.01);
(Continued)

(58) Field of Classification Search
CPC . B05B 17/06; B05B 17/0607; B05B 17/0638; B05B 17/0646; B05B 17/0653;
(Continued)

(56) References Cited

U.S. PATENT DOCUMENTS

2002/0129813 A1* 9/2002 Litherland .............. B05B 15/14
128/200.16
2004/0004133 A1* 1/2004 Ivri ...................... A61M 11/007
239/11

(Continued)

FOREIGN PATENT DOCUMENTS

DE 30 13 964 A1 10/1981
WO 2009/118717 A1 10/2009
(Continued)

OTHER PUBLICATIONS

International Search Report dated Oct. 29, 2018 in International Application No. PCT/EP2018/072824 (4 pages).
(Continued)

Primary Examiner — Cody J Lieuwen
(74) Attorney, Agent, or Firm — Bookoff McAndrews, PLLC (57) ABSTRACT

An aerosol delivery system has an aerosol generator with a vibrating aperture plate (10) and an actuator (11, 16, 17, 19), a controller (18, 19). The controller in real time monitors (201) the aerosol generator as it is driven for vibration of the aperture plate, and detects (202) a change in an electrical characteristic in response to a transition from a wet state to a dry state of the aperture plate. It automatically modifies (203, 205, 206), during the transition, operation of the aerosol generator in response to the detected change. The modification includes reducing applied power (203). The controller continues (204) to monitor during the transition, including monitoring the aperture plate for presence of residual liquid on the aperture plate first surface. The con-
(Continued)

troller monitors at a number of drive frequencies and maintains data representing trends in a combination of the electrical characteristic signals at the different frequencies, and identifies a start of a transition if a calculated value rises above a threshold. There is one threshold for triggering a check scan for residual volume and a higher threshold to trigger an immediate shut down.

21 Claims, 10 Drawing Sheets (51) Int. Cl.
    *B05B 17/00*     (2006.01)
    *B05B 17/06*     (2006.01)
    *A61M 15/00*     (2006.01)

(52) U.S. Cl.
    CPC ...... *B05B 17/0646* (2013.01); *B05B 17/0669* (2013.01); *A61M 2205/3317* (2013.01); *A61M 2205/50* (2013.01)

(58) Field of Classification Search
    CPC ............. B05B 17/0667; B05B 12/081; A61M 11/005; A61M 15/0085; A61M 2205/3317; A61M 2205/50
    See application file for complete search history.

(56) References Cited

U.S. PATENT DOCUMENTS

| | | | |
|---|---|---|---|
| 2006/0102172 A1 | 5/2006 | Feiner et al. | |
| 2010/0089395 A1* | 4/2010 | Power | A61M 16/0666 128/203.15 |
| 2012/0291777 A1* | 11/2012 | Gordon | B05B 17/0646 324/649 |
| 2015/0231340 A1* | 8/2015 | Pumphrey | B05B 17/0646 128/200.16 |

FOREIGN PATENT DOCUMENTS

| | | |
|---|---|---|
| WO | 2010/035251 A2 | 4/2010 |
| WO | 2010/035251 A3 | 4/2010 |
| WO | 2014/062175 A1 | 4/2014 |
| WO | 2015/010809 A1 | 1/2015 |
| WO | 2015/091356 A1 | 6/2015 |
| WO | 2017/055166 A1 | 4/2017 |

OTHER PUBLICATIONS

Written Opinion of the International Searching Authority dated Oct. 29, 2018 in International Application No. PCT/EP2018/072824 (10 pages).

Notice of Opposition in European Patent Application No. 18755498.5, dated Jun. 22, 2022 (19 pages).

* cited by examiner

```
                    Frequency Hopping
                    ┌──────────────────┐
                    │    127,128 & 129 │
                    │         kHz      │
                    └──────────────────┘
                    Frequency Hopping
```

Set FREQ_128kHz delay_ms(2)

Read SHUNT_VOLTS128KHZ

Set FREQ_127kHz delay_ms(2)

Read SHUNT_VOLTS127KHZ → G_average127 → G_sum OfDifferences127

Set FREQ_128kHz delay_ms(2)

Read SHUNT_VOLTS128KHZ → G_average128 → G_sum OfDifferences128

Set FREQ_129kHz delay_ms(2)

Read SHUNT_VOLTS129KHZ → G_average128 → G_sum OfDifferences129

Record

+

+

=

ASO shuts off power to nebulizer when activated

ASO
G_combined SumOfDifferences

Fig.11

PROTECTION OF APERTURE PLATE DURING AEROSOL GENERATION

CROSS-REFERENCE TO RELATED APPLICATIONS

This patent application is the U.S. national phase entry under 35 U.S.C. § 371 of International Application No. PCT/EP2018/072824, filed Aug. 23, 2018, which claims the benefit under 35 U.S.C. § 119 to European Application No. 17188034.7, filed on Aug. 25, 2017, the entireties of which are incorporated herein by reference.

INTRODUCTION

Field of the Invention

The invention relates to aerosol generators (or "nebulizers") and the delivery of aerosol medication.

Prior Art Discussion

Aerosol generators generally comprise a vibratable member ("aperture plate", "AP") having a plurality of apertures extending between a first surface which is adapted to receive a liquid to be aerosolised and a second surface at which an aerosol is generated. The aperture plate may be vibrated using a piezoelectric element which receives power and mechanically vibrates in order to convert the liquid on the first surface of the aperture plate to aerosol at the second surface.

One such device is described in our WO2012/046220A, which describes an aerosol generator with an aperture plate or membrane which is supported by a washer in a housing. The aperture plate is driven by a piezo element actuator. The aperture plate is vibrated at high frequency, typically 127 to 157 kHz, and this action breaks the surface tension of the liquid and creates an aerosol plume of droplets. Such systems are commonly called vibrating mesh technology.

The aperture plate is operated until the medication has been fully aerosolized. Arrangements to detect end of dose are described in WO2014/062175 (Nektar), and the following published patent specifications of the present applicant also describe arrangements to detect end of the dose: WO2015/010809, WO2010/035251, WO2009/118717, and WO2017/055166.

Due to the high-frequency operation there is a risk of damage to the AP while running at a high level of actuating power, such as is required for certain uses to for example emit a dose of greater than 1 ml/min. Hence, frequent inspection is required and/or aperture plate precautionary replacement before it is necessary.

The invention addresses this problem.

SUMMARY OF THE INVENTION

It has been found by the inventors that as the aerosol aperture plate transitions from a wet state to a dry state, it comes under increased mechanical stress and this may have an adverse effect on the durability of the nebulizer, significantly shortening its operational life due to cracking/fracturing of the aperture plate. This problem is particularly serious if the aerosolization output of the nebuliser is increased—the increased power applied to the nebuliser increases the risk of damage to the aperture plate.

The plate can be operated in the dry state at full power with little or no damage and similarly, it can be operated at full power in the wet state with little or no damage. However, the sudden change in displacement at the instant of the plate changing from wet to dry can cause damage. Such stress may, over time, result in cracking/fracturing of the aperture plate.

In various embodiments an aerosol delivery system has an aerosol generator with a vibrating aperture plate and an actuator, a controller. The controller in real time monitors the aerosol generator as it is driven for vibration of the aperture plate, detects a change in an electrical characteristic in response to a transition from a wet state to a dry state of the aperture plate; and automatically modifies, during the transition, operation of the aerosol generator in response to the detected change. The modification may include reducing applied power. The controller continues to monitor said change during the transition, including monitoring the aperture plate for presence of residual liquid on the aperture plate first surface. The controller monitors the electrical characteristic (such as drive current) at a number of drive frequencies and maintains data representing trends in a combination of the monitored characteristic signals. It may identify a start of a transition if a calculated value derived from the monitored signals rises above a threshold. There is one threshold for triggering a check scan for residual volume and a higher threshold to trigger an immediate shut down.

The invention effectively protects the aperture plate by performing this method in real time. Importantly, it identifies a transition of the AP to dry and hence predicts the plate becoming dry and takes appropriate action in advance. This may be reducing power or shut down, depending on the extent of residual liquid. The aspect of using a real time derived or calculated value which magnifies the changes in individual monitoring signals allows very prompt identification of a transition. By switching from the normal drive cycle to a short scan of only 5 measuring points it can promptly in real time identify whether there is residual liquid. The result of the invention is a major reduction in risk of damage to the AP, and hence improved operation of an aerosol generator or nebulizer during its life cycle.

Various aspects of the system and method are as set out herein, including aspects of the aerosol generating system and aspects of the controller method performed in real time.

ADDITIONAL STATEMENTS

According to the invention there is provided a method of operating an aerosol delivery system comprising an aerosol generator and control means for controlling the operation of the aerosol generator wherein the aerosol generator comprises a vibratable member having a plurality of apertures extending between a first surface which is adapted to receive a liquid to be aerosolised and a second surface at which an aerosol is generated, wherein the method comprises the steps of:—

- determining at least one electrical characteristic of the aerosol generator;
- monitoring a change in the electrical characteristic in response to a transition between a wet state and a dry state of the vibratable member; and
- modifying the operation of the aerosol generator in response to the change in the electrical characteristic during the transition between the wet state and the dry state of the vibratable member.

In one embodiment the modification is a reduction in the power applied to the vibratable member.

In one case the operation of the aerosol generator is modified automatically upon detection of the transition.

In one embodiment the method comprises continuously monitoring the change in the electrical characteristics of the aerosol generator throughout the transition.

The method may comprise continuously reducing the applied power to the vibratable member in response to the change in electrical characteristics.

In one case the method comprises monitoring an electrical characteristic of the aerosol generator prior to the transition from wet to dry.

The method may comprise monitoring an electrical characteristic of the aerosol generator and comparing the electrical characteristics of a plurality of readings to predict an imminent change from wet to dry.

In one embodiment the method comprises monitoring the electrical characteristic at an operating frequency and at one or more one other frequency adjacent to the operating frequency, and preferably the aperture plate is driven at these frequencies in time division multiplexing cycles.

A frequency within 5 kHz of the operating frequency may be used. In one case the method comprises monitoring the electrical characteristic at a first frequency less than 5 kHz below the operating frequency and at a second frequency less than 5 kHz above the operating frequency to determine if a change has occurred. A first frequency about 1 kHz below and a second frequency about 1 kHz above the operating frequency may be used, in one case.

In one embodiment, the control means monitors signals representing the electrical characteristic at each of the drive frequencies and maintains data representing trends in each signal and/or in a combination of the signals, and identifies a start of a transition if a calculated value representing deviation from said trend or trends rises above a threshold.

The duration of at least some, and in one case all, of the monitoring steps is small in the order of ms such as 2 ms, and preferably in the range of 1 ms to 4 ms.

The monitoring step may be performed by a processor executing an algorithm which determines a trend in the electrical characteristic, such as drive current. This builds up an operating profile. If there is even a small deviation from this trend it may immediately detect the start of a transition. The output of the algorithm is typically steady, but has an exaggerated jump when the transition starts. If the electrical characteristic is monitored at each of a number of drive frequencies in a time division multiplexed manner there may be two electrical characteristic changes simultaneously, thereby allowing immediate detection. This may, for example, be an increase in drive current at one drive frequency and a decrease in drive current at a different frequency.

In one embodiment the method comprises shutting off the applied power to the aerosol generator when the transition is about to complete.

The method may comprise monitoring the vibratable member for the presence of residual liquid on the first surface. The method may comprise activating power at a low level in response to detection of residual liquid on the first surface. The method may comprise activating the power incrementally until the residual liquid is aerosolised. The method may comprise monitoring the vibratable member in order to detect when the first surface is in a dry state and indicating confirmation that the remaining liquid has been aerosolised. The method may comprise shutting off power to the aerosol generator upon detection of the dry state.

The invention also provides an aerosol generator delivery system comprising an aerosol generator and control means for controlling the operation of the aerosol generator, the aerosol generator comprising a vibratable member having a plurality of apertures extending between a first surface which is adapted to receive a liquid to be aerosolised and a second surface at which an aerosol is generated, wherein the control means is configured to:
- determine at least one electrical characteristic of the aerosol generator;
- monitor a change in the electrical characteristic in response to a transition between a wet state and a dry state of the aperture plate; and
- modify the operation of the aerosol generator in response to a change in the electrical characteristic during the transition.

In one case the controller is configured to modify the operation of the aerosol generator by a reduction in applied power to the aerosol generator In one embodiment the controller is configured to automatically reduce the power upon detection of the transition. The controller may be configured to continually monitor the changing electrical characteristics of the aerosol generator throughout the transition. The controller may be configured to continually reduce the applied power to the aperture plate in response to the change in electrical characteristics.

The controller may be configured to monitor the electrical characteristics of the aerosol generator to detect when the aperture plate prior to the transition from wet to dry.

The controller may be configured for monitoring an electrical characteristic of the aerosol generator and comparing the electrical characteristics of a plurality of readings to predict an imminent change from wet to dry.

In one case the controller is configured for monitoring the electrical characteristic at the operating frequency and at one or more other frequency adjacent to the operating frequency. In one case the controller is configured for monitoring the electrical characteristic at a frequency within 5 kHz of the operating frequency.

In one embodiment the controller is configured for monitoring the electrical characteristic at a first frequency less than 5 kHz below the operating frequency and at a second frequency less than 5 kHz above the operating frequency to determine if a change has occurred.

In one case the controller is configured for monitoring at a first frequency about 1 kHz below and at a second frequency about 1 kHz above the operating frequency.

The duration of at least some, and in one case all, of the monitoring steps is small in the order of ms such as 2 ms.

In one embodiment the controller is configured to automatically shut off the applied power to the aperture plate when the transition is complete. The controller may be configured to monitor the aperture plate in order to detect residual liquid on the plate. If residual liquid is detected, the controller may be configured to activate power to the plate at a low level. The controller may be configured to activate the power in increments until the aperture plate is in a dry state. The controller may be configured to monitor the plate in order to detect when the aperture plate is in a dry state.

In one case the controller is configured to indicate end of dose upon detection of the dry aperture plate. The controller may be configured to shut off power to the aperture plate at end of dose.

In one case the controller has a processor programmed to execute an algorithm as set out above in any embodiment.

BRIEF DESCRIPTION OF THE DRAWINGS

The invention will be more clearly understood from the following description of some embodiments thereof, given by way of example only with reference to the accompanying drawings in which:—

DETAILED DESCRIPTION

Figure 1:
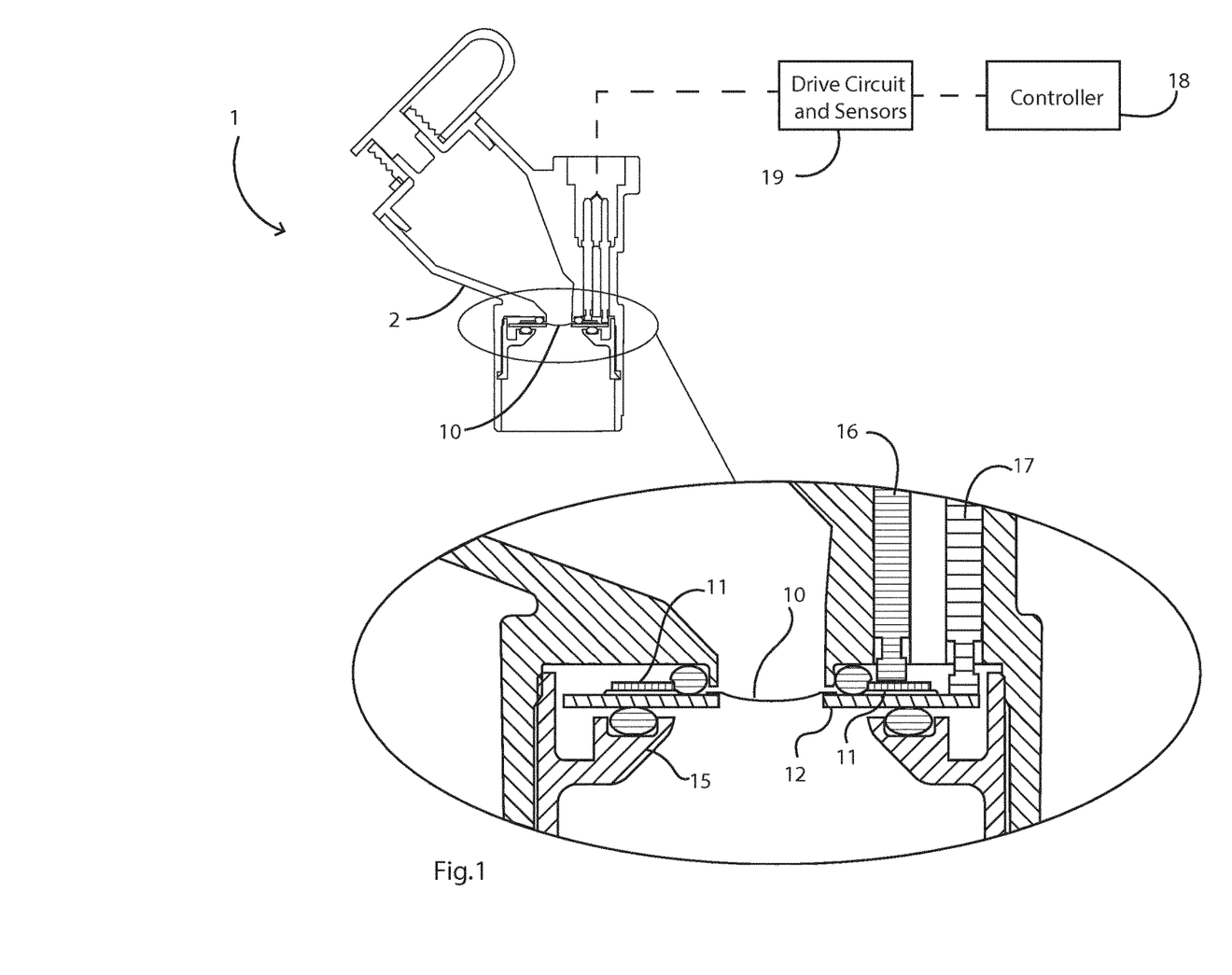
FIG. 1 is a diagrammatic view of a nebulizer.

Referring to FIG. 1, an aerosol delivery system 1 comprises an aerosol generator with an aperture plate or membrane 10 which is supported in a housing 15 by a washer 12 also supporting an annular piezo element actuator 11. A drive pin 16 is in contact with the top surface of the actuator 11 and a drive pin 17 is in contact with the washer 12, so that power is applied across the actuator 11 directly to the top surface by the pin 16 and via the washer 12 to the bottom surface from the pin 17. A controller 18 includes a digital processor which is programmed to control a drive circuit 19 which delivers power to the pins 16 and 17. The drive circuit includes shunt voltage sensors to monitor current supplied to the pins 16 and 17. The processor is programmed to control the drive signals so that the aperture plate is driven at each of a number of drive frequencies in cycles, as described in more detail below.

Figure 2:
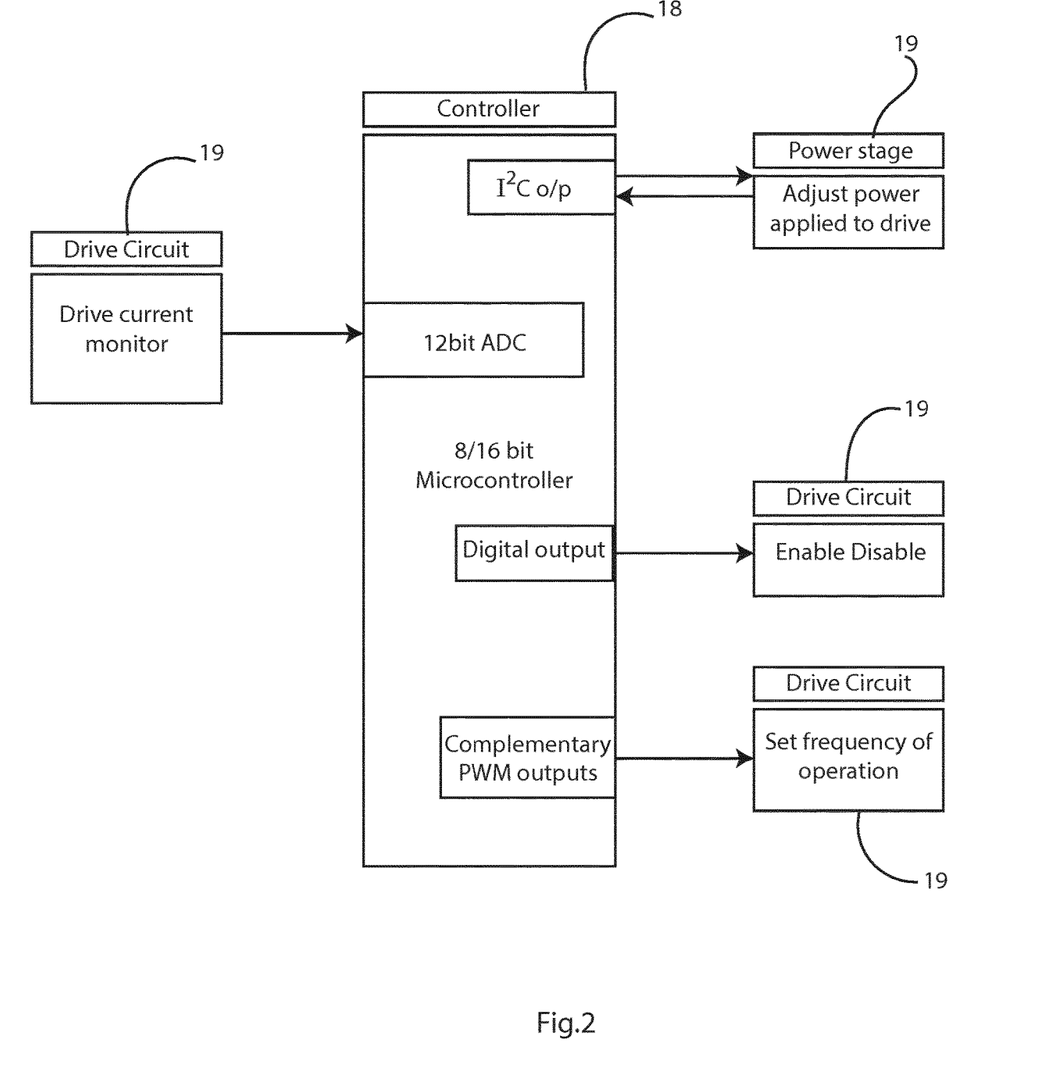
FIG. 2 is a more detailed view of the controller and drive circuit.

The hardware arrangement is illustrated in more detail in FIG. 2. The controller 18 comprises an 8-bit (or in other embodiments a 16-bit for example) microprocessor. A controllable voltage source is provided to allow adjustment of power to the AP. A drive stage applies an AC signal to the piezo actuator 11 via the pins 16 and 17. A pulse width modulator (PWM) output from the microprocessor controls frequency of operation, a current sense module provides power feedback, and an enable/disable pin of the microprocessor switches on and off the power.

The aperture plate is vibrated at high frequency of typically 127 to 157 kHz and this action breaks the surface tension of the liquid and creates an aerosol plume as droplets pass through the aperture plate.

In general, the aperture plate continues vibrating throughout the delivery of the aerosolised liquid. However, we have found that as the first surface of the aperture plate transitions from a wet state to a dry state, the aperture plate experiences increased mechanical stress. If allowed to continue this would have an adverse effect on the durability of the aerosol generator, significantly shortening its operational life, due to cracking or fracturing of the aperture plate. This is the case even if power is shut off before the plate becomes dry.

Figure 3:
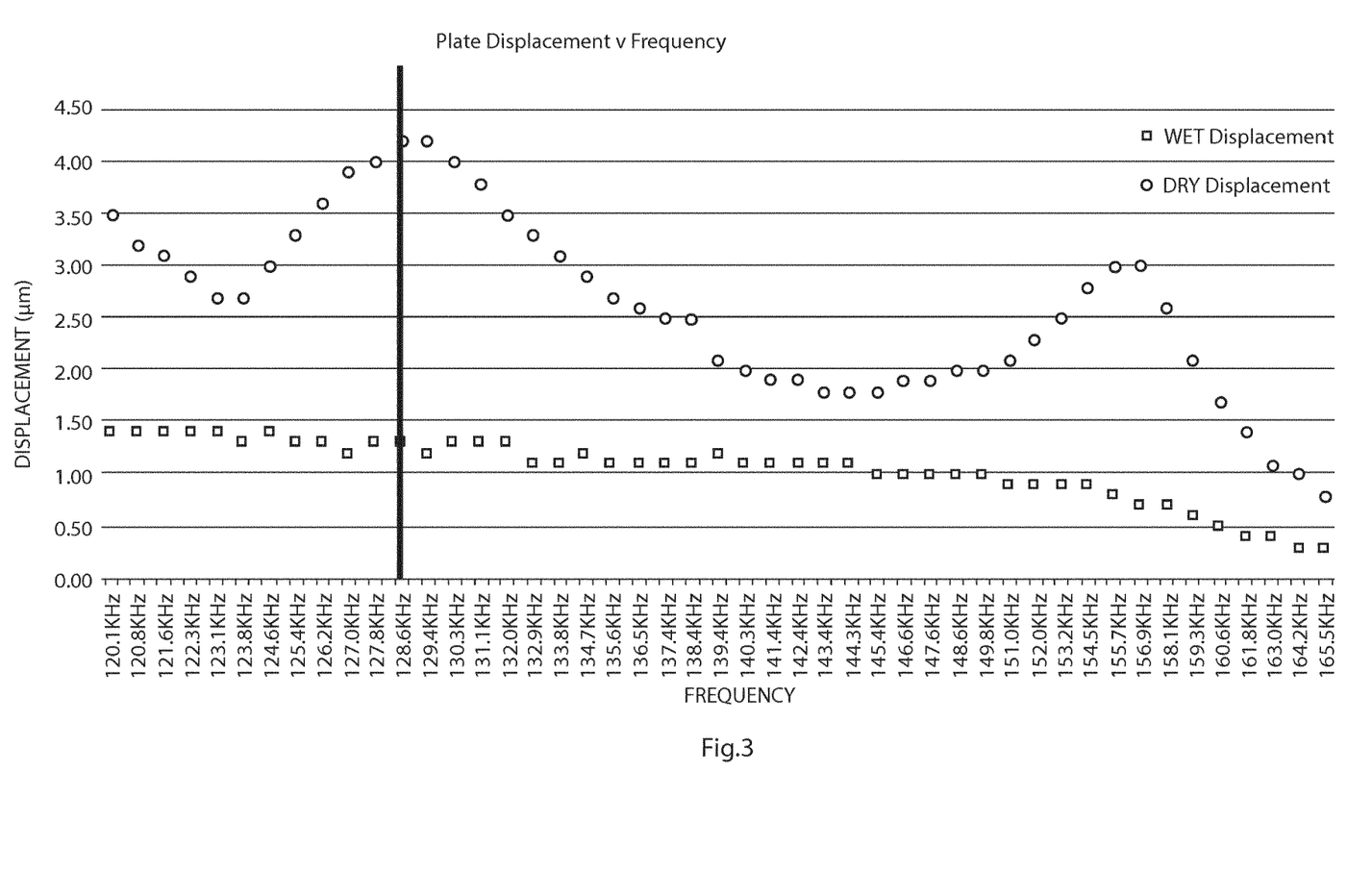
FIG. 3 is an illustration of the displacement of an aperture plate across a range of drive frequencies when the plate is wet (lower line) and when dry (upper line)

FIG. 3 is a pair of plots of aperture plate displacement vs. drive frequency, one for a wet plate and one for a dry plate. The vertical line indicates the difference for a drive frequency of 128 kHz, about 1 µm when wet and about 4 µm when dry. Hence if the plate transitions from wet to dry when being driven at this frequency the displacement will increase until there is a four-fold increase in displacement. We have found that the transition to dry can cause considerable damage to the plate as it changes to the much higher displacement. Operation in a constant wet or dry environment does not cause the same effect on life of the aperture plate.

This may be a particular problem in delivery of aerosolized medication where it is necessary to increase the aerosolization output from for example 1.0 ml/min, by increasing the power applied to the actuator from for example 1.2 Watts to 2.0 Watts. The damaging stress on the aperture plate may be particularly high during transition from a wet state to a dry state in these circumstances.

The aerosol delivery system (or "nebulizer") reduces mechanical stress on the aperture plate during transition from wet to dry, i.e. in advance of it becoming dry, as set out in more detail below.

The digital processor is programmed to execute an algorithm which monitors AP applied power consumption to detect start of transition of the aperture plate from wet to dry, in effect giving an early prediction of the AP dry state. Upon detection of the start wet to dry transition the controller is configured to automatically reduce the power applied to the aperture plate. The reduction may be partial or complete, either immediately upon detection of the start of the transition or during the transition. The controller 18 performs this monitoring and control in real time, by automatically detecting small changes in the electrical characteristics of the aerosol generator. The controller in one example predicts an imminent change of state from wet to dry and removes power from the device prior to the plate reaching a complete dry state.

In some cases the method comprises monitoring of the electrical parameters in combination with utilizing a software method to perform calculations to determine a derived calculated value in real time for determining the status of the plate. The derived calculated value is referred to also in this specification as the "numerical output".

Figure 4:
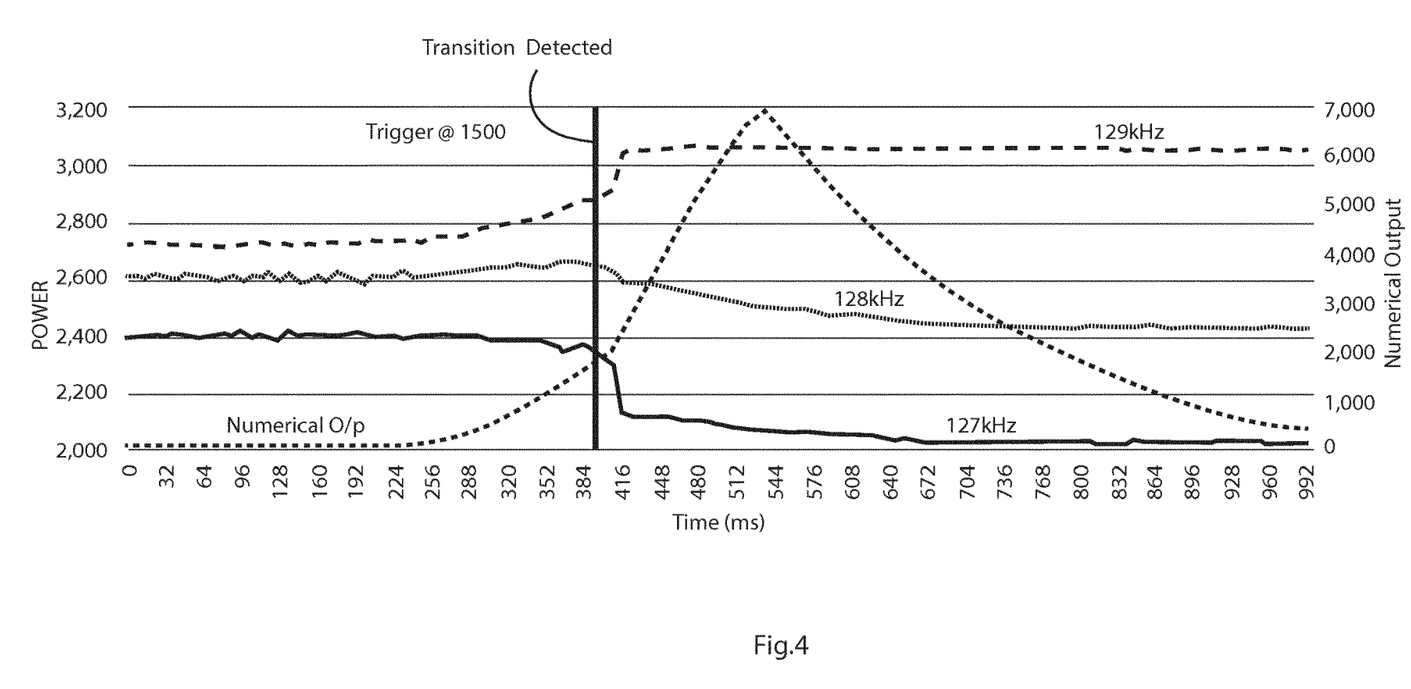
FIG. 4 is a set of plots showing drive current (proportional to power delivered to the plate) for each of three drive frequencies, and also the numerical output of a processor algorithm which processes the data of the three plots to provide an indication of start of transition from wet to dry.
Figure 5:
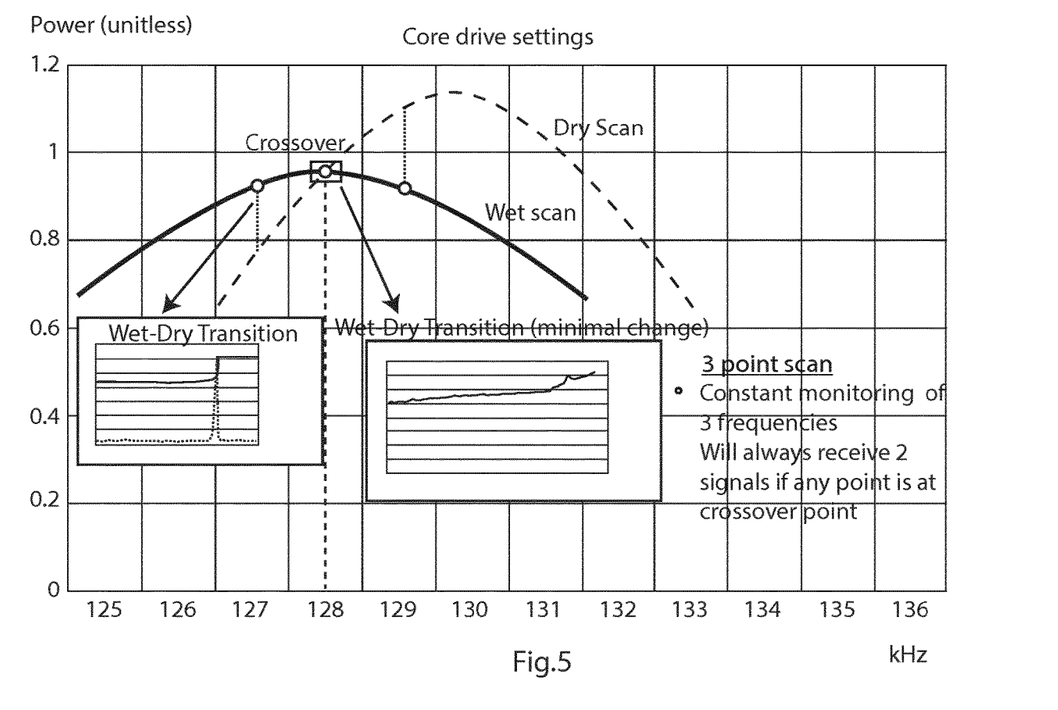
FIG. 5 is a set of plots indicating benefit of using three drive frequencies for predicting transition to dry.

FIG. 4 shows the power consumed by the aerosol generator (based on drive current because voltage is static) over time for a drive frequency of 129 kHz (top line), 128 kHz (middle line), and 127 kHz (bottom line). In one example the plate is driven at each of these three frequencies in turn in a cyclic manner, with the drive at each frequency being for about 2 ms, hence the drive at each frequency is for about 256 vibration cycles of the plate. The centre frequency may be termed the operating frequency and the upper and lower as first and second frequencies. In other embodiments the drive scheme may be different. For example, the differences between the drive frequencies may be more than 1 kHz, possibly up to 5 kHz. Also, the duration at each frequency may be different from 2 ms, for example a value in the range from about 1 ms up to about 20 ms. The applied power is provided at a fixed DC voltage, such as 15 V. The power consumed varies according to the AP status, and this is in many embodiments detected by monitoring current drawn using a shunt resistor. The power consumption values are used as inputs to an algorithm which provides in real time the numerical output. The algorithm, as described in more detail below, provides the numerical output with an exaggerated change in comparison to the sensed values. As shown in FIG. 4 the power drawn rises for one frequency but reduces for the other two, and the extents of change are different. The algorithm uses these seemingly contradictory signals to provide a single numerical output which rapidly changes, thereby allowing real time dry state prediction and hence real time control of the AP drive to avoid damage to the AP as it transitions to the dry state. In FIG. 4 the left hand vertical axis is power as represented by units derived from the drive circuits. This may be measured for example by measuring voltage across a shunt resistor. The right hand vertical axis is the numerical output referred to above.

The vertical line near the centre of FIG. 4 shows the point at which the processor detects the start of transition and hence predicts the dry state. According to the settings the controller may reduce power or it may remove power at this time (about 390 ms from the start of this test). The processor algorithm numerical output begins to increase and once a predetermined value (in this case 1500) is reached, the controller will take an action as determined by either a profile setting or a scan to verify that there is a transition to dry. The action is to prevent the AP from reaching its final dry state, or allow it to become dry with incremental reductions in power so that damage is prevented. It is expected that the residual volume remaining at the transition detection will be only in the range of 0.5% to 5% of the original volume (dose).

The digital processor of the controller is programmed to dynamically, in real time, monitor all three traces according to the algorithm, so that it can immediately detect the start of the transition to dry.

Referring to FIG. 5, the benefit of the cyclic multi-frequency drive is illustrated. A single frequency point scan would run the risk of having little change when the plate transitions between wet and dry, because the actuator power consumption signals for wet and dry cross over. In the specific example of FIG. 5 this crossover frequency is about 128 kHz, however it may be different for not only different APs but also for different liquid viscosities. The fact that the algorithm uses a 3-point scan method avoids risk of such an occurrence, the numerical output being an exaggerated value based on multiple signals each changing in their own way. FIG. 5 shows diagrammatically the differences in power consumption for different frequencies (X-axis is frequency, kHz; and Y-axis is power, no units). In general, the Y-axis may be measured as shunt voltage, current or power (depending on measurement technique). These are related and will show a similar change when the AP starts to transition from wet to dry. The X-axis is the frequency range in kHz. By using the algorithm when one point is on the crossover (showing little or no change between wet and dry), the other two points will receive a larger signal change at the start of transition. The algorithm takes the baseline value and integrates the area under change from all three resulting in excellent sensitivity to the transition.

The algorithm output signal line shows a low background level while the plate is wet. However, as it starts to become dry there is a spike in the line signal, and the ramp time is in this example from about 224 ms to 530 ms. For the 129 kHz line there is step change to an increased electrical power consumption (indicated by an increase in drive current drawn). However, for the 128 kHz line there is little change in drive current, merely a deviation which appears like low-level noise. However, at some frequencies this is a reduction in power at the change, and this is the case for the 127 kHz plot. The change in electrical power is an indication of the plate transitioning to running dry which results in a large jump in displacement. This stepped change in input power and hence aperture plate mechanical power shows how the transition from wet to dry results in more mechanical exertion and damage on the aperture plate.

The algorithm predicts (based for example on monitoring a number of drive current previous readings such as 8 previous readings) an imminent change of state from wet to dry and once this has been determined, the controller reduces or removes power from the actuator prior to the plate reaching a completely dry state. The algorithm exaggerates the small changes in drive current and by monitoring trends deviations from the current trends it detects very small deviations at one, two, or all three frequencies. In this example it will only detect significant changes for the 129 kHz and 127 kHz frequencies. This illustrates an important advantage arising from having multiple frequencies; if there is a late response to start of transition at one of them, there is still likely to be a good discernible change at one or more of the others. In any event, the algorithm uses all of the changes irrespective of their direction or extent. It is not possible to know in advance which is the most useful one, as this depends on the nature of the liquid (typically including a drug) being aerosolised and other conditions which are not known in advance.

The processor algorithm may operate even for only a single drive frequency because of the numerical generation of a trend and consequent early detection of a change above a threshold.

In use, when an imminent change of state of the aperture plate from wet to dry has been determined by the controller, the power applied to the aperture plate by the actuator is reduced prior to powering off the aperture plate completely. This stage is implemented at the start of the transition of the plate from wet to dry. This results in a reduction in the step change and significantly reduces the mechanical stress experienced by the aperture plate when in a dry state. Furthermore, this results in an increase in the life of the aperture plate.

The wet to dry transition may be identified by utilizing the data from the plot of FIG. 4; the algorithm uses the electrical characteristics during normal delivery to generate an "operating" profile. Any event that is uncharacteristic of this operating performance indicates a change of state. For example, a number of previous readings, such as eight readings, are used to predict an imminent change from wet to dry.

As noted above, it is particularly advantageous that even if a minimal change in electrical characteristics exists at the operating frequency, one or both of the side frequencies will record a change sufficient to identify the wet-dry transition as illustrated in FIG. 4.

In the illustrated example, the drive is at 128 KHz for a short time such as 2 ms, it then changes frequency to 127 kHz for a short time such as 2 ms to determine if a change has occurred. It then reverts back to 128 ms for a short time such as 2 ms before checking at 129 KHz for a short time such as 2 ms. It continually follows this short sequence. However, the frequency values, the durations at each, and indeed the number of different frequencies used may be different.

The time spent at the two side frequencies has no discernible effect on flow rate, because this time is very short. A response will be detected at one or more frequencies when a change from wet to dry occurs. The wet to dry transition occurs over a period of about 100 ms to 300 ms. The controller checks the drive current status at the three frequencies multiple times within the transition duration, ensuring that the change is identified and acted upon prior to the device going completely dry.

Figure 6:
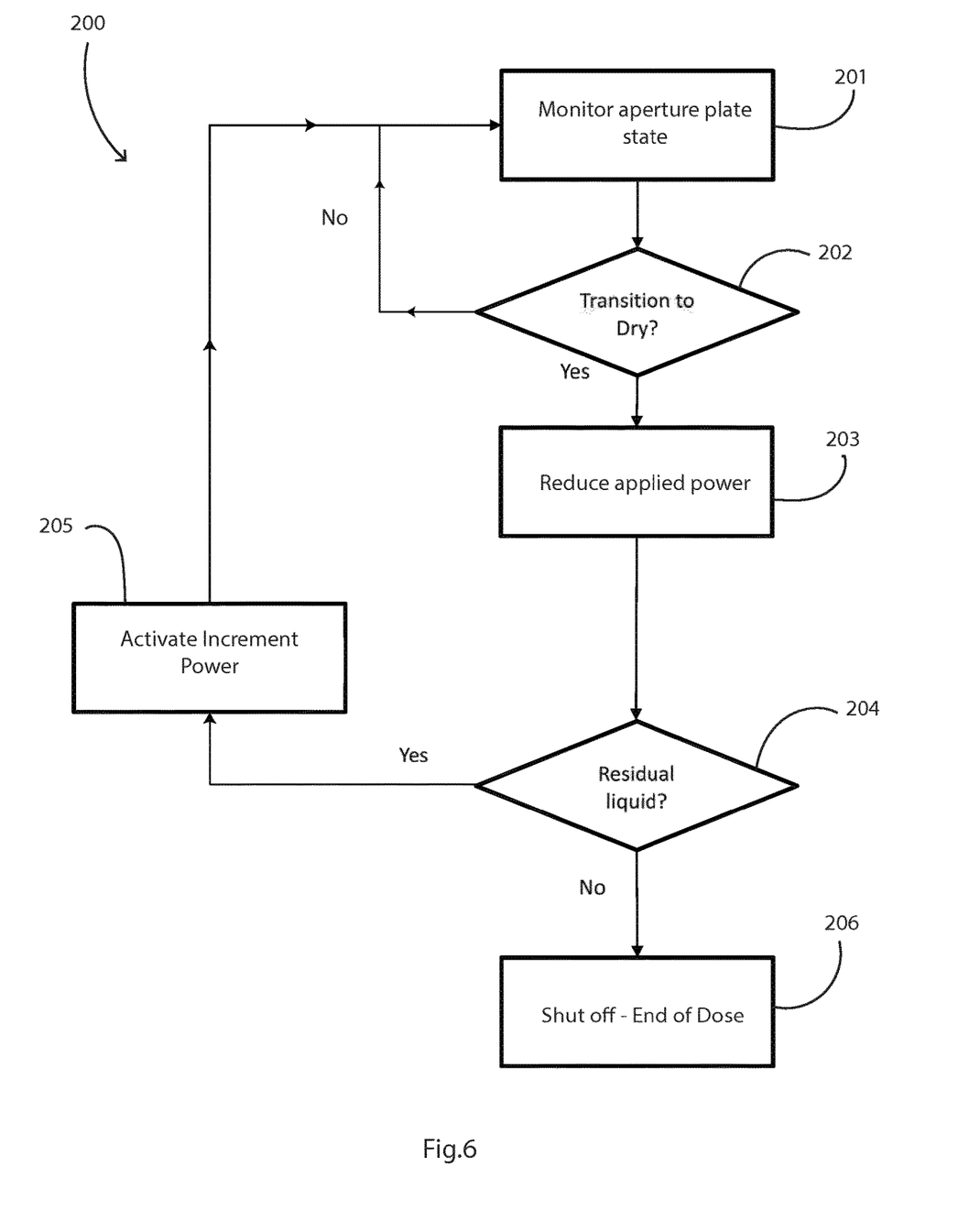
FIG. 6 is a flow diagram of controller operation for one example of operation.
Figure 7:
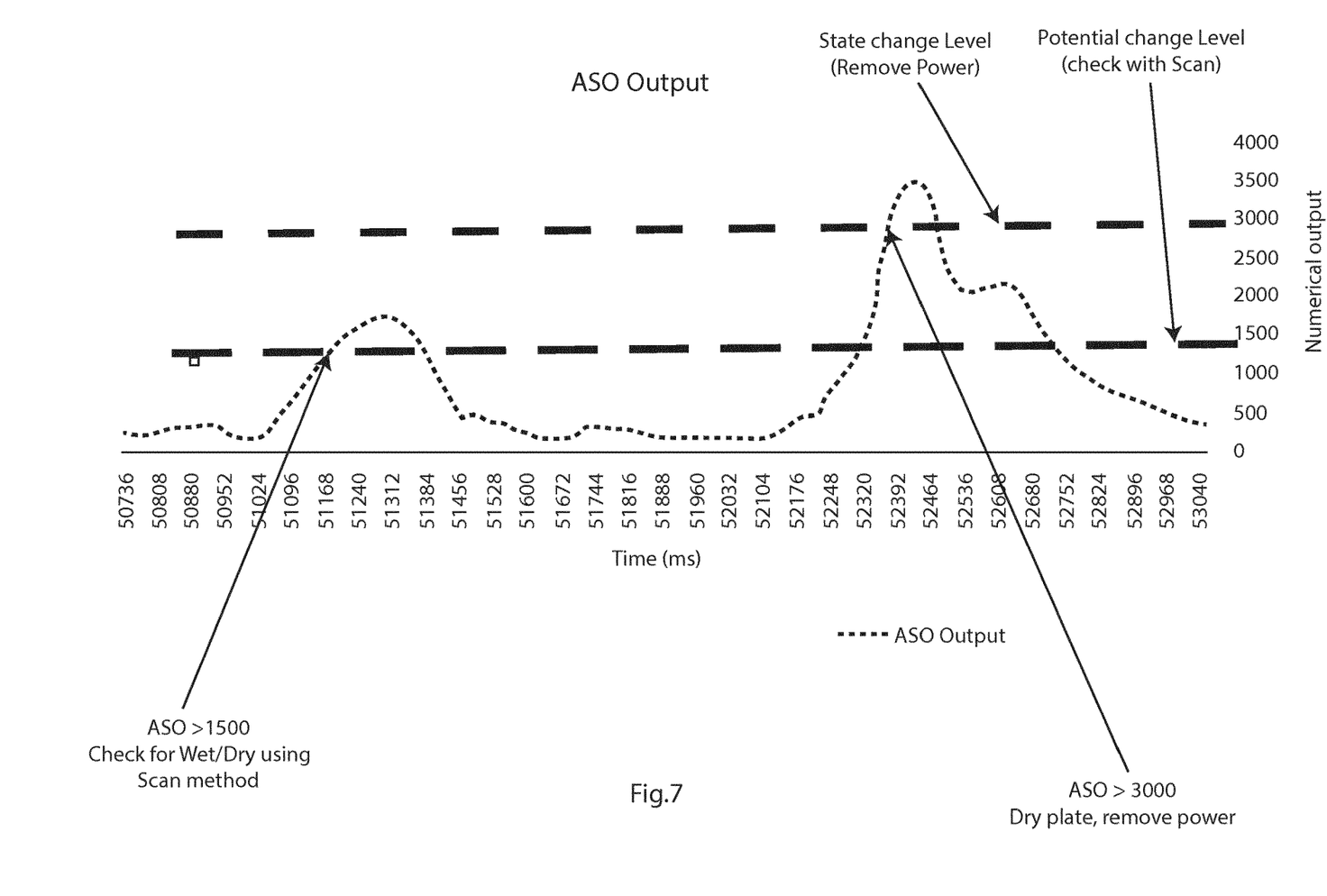
FIGS. 7 and 8 are plots for performance of some steps of the flow.
Figure 8:
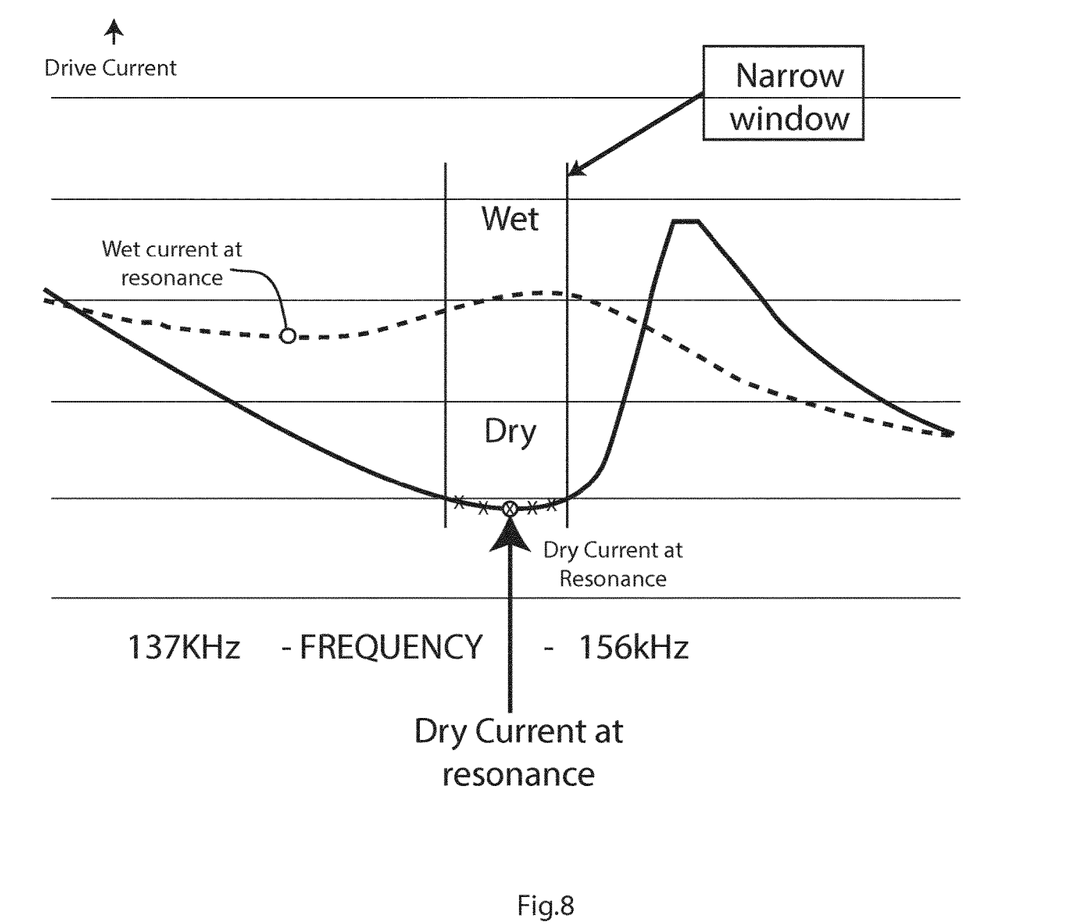

Referring to FIGS. 6 to 8, a method 200 of the invention may have steps 201 to 206 as follows:

201, monitor aperture plate state;
202, check if the transition of the plate from wet to dry started;
203, reduce applied power to the plate if the numerical output exceeds a first threshold;
204, check if there is residual liquid on the plate;
205, if so, activate plate at incrementing power; and
206, if not, shut off power.

The flowchart shows a series of steps and stages involved in the completion of the dosage required to be nebulized. The aperture plate state is monitored in order to determine if the transition from wet to dry has started. If not, this loop is repeated. If the transition has started, the power to the actuator is reduced. The aperture plate is then monitored to check if residual liquid is still present on the plate. If there is liquid present, a low level of power increment is activated. The aim of this stage is to nebulize the remaining droplet of liquid at the minimum power level required, and therefore minimal stress for the aperture plate during the wet to dry transition prior to confirming the status by dry detect indication. This loop is repeated until there is no residual liquid detected, whereby end of dose is detected and power to the plate is shut off. In other embodiments the step 205 increases the power back to the full level for faster aerosolization of the residual liquid, subject to the checks of steps 201 and 202.

The flow may also include an initial determination at power-up if the AP is wet, upon which the actuator continues with the step 201 with cycling across the three frequencies of 127 kHz, 128 kHz, and 129 kHz until the transition is detected. Hence, the controller will immediately shut off when powered up as a protection measure if the plate is dry to begin with. This initial check is preferably made with minimum power applied to the AP actuator. This "wet detect" step makes a, low voltage ($10y$), wet/dry determination based on the plate response at a frequency close to the natural frequency of the aerosol generator, within a band of +/−2 kHz around the natural frequency. Upon detection of liquid at startup, the generator is activated at 15V. The drive frequency changes every 2 ms alternating from +/−1 kHz around the center frequency of 128 kHz in a cyclic manner (frequency hopping). After an initial settling time of 160 ms, the controller begins to monitor the plate response at the three operating frequencies (127, 128 & 129 kHz)

FIGS. 7 and 8 provide more detail about the steps 204 and 205. FIG. 7 shows two events as follows.

The numerical output ("ASO") value exceeds a trigger level of 1500 at about 51168 ms in this example. This causes the step 202 detection and the step 203 reduction of power to 10V. The controller then performs a scan in a manner such as described in WO2015/010809. This is a scan with multiple measuring points, at each of which there is a different drive frequency and drawn current is measured. The drive current readings for the scan allow the processor to determine if there is residual liquid on the AP, for performance of step 204. In this case the number of measuring points is low, as shown in FIG. 8 only five. The scan in the example of FIG. 8 shows typical plots for wet (higher drive current, but is sloping downwards), and dry (sloping upwards).

After the scan is performed the controller reverts to the three-point cyclic drive as represented by the steps 201 and 202. In another embodiment, the controller may alternatively continue with one or more subsequent scans to repeat step 204. In doing so it is continuing with aerosolizaton (albeit with a non-optimal drive scheme) and detecting further transition very quickly.

After reverting to steps 201 and 202, if the numerical output value exceeds a "state change" trigger or threshold level of 3000 (shown to the right of FIG. 7) it shuts off power. Referring to the FIG. 6 logic flow, this is effectively step 203 being reduction to OFF, step 204 indicating no residual volume, and shut off in step 206.

The start of a change of state can be seen close to 52180 ms into the delivery cycle, and the controller shuts off at 52380 i.e. 200 ms after a change began. The device would have taken another 300 ms to go completely dry i.e. it would have been fully dry at 52680 ms.

The ASO removes power while there is still a very small volume of liquid, about 6 μl, on the plate, therefore preventing the displacement of the plate from reaching levels in the range of 4 μm to 6 μm seen when completely dry The controller is preferably pre-set with values representing AP resonant frequency, a range of current for a wet state, and a range of currents for a dry state. This scan is completed in a very short period of time (20 ms) to ensure minimal interruption to plume. This scan for step 204 is preferably run at reduced power, for example dropping from 15 V to 10 V, to avoid any damage to the plate.

In one example, mode of operation, after the first step 204 scan the controller may return to normal run mode at 15V, then stops after a period such as 160 ms and repeat the scan. It will keep on checking in this way until the ASO value returns below the lower threshold of 1500.

Whether there is one scan or multiple in series, by use of the two threshold levels the controller accurately determines if a step 202 is only noise (left peak of FIG. 7) or a real transition (right peak of FIG. 7).

The flow of FIG. 6 provides a reliable system, capable of durable high-power delivery utilizing existing nebulizer technology. It advantageously determines the status of the plate prior to informing the user of the dose completion. Advantageously, the nebulizer allows for high-power to be applied to aperture plates, where higher dose levels are required, whilst mitigating against the mechanical stress that occurs on the plate when transitioning from the wet to dry state. Furthermore, by eliminating or reducing this mechanical stress, the aperture plate life is extended with minimal changes in electrical parameters.

The accuracy of the modes of the invention is extremely important as it is often very important that the patient receive a complete dose of medication. The risk of false triggering can result in a partial dose delivery, which is highly undesirable.

The invention thereby prevents cracking or fracturing of aperture plates and thereby extends the life of aperture plates.

The algorithm was tested on 15 samples on a bench top test. The 15 samples went through 10 cycles using 0.9% saline. Each sample was monitored to ensure that a full dose was delivered and after the dose was completed the aerosol generator would automatically power down. All samples passed. The test checks that the aerosol generator has a minimum life expectancy of 1.5 years equating to 92 hours of operation, or 5475 doses. This was achieved for all of 30 test devices.

Figure 9:
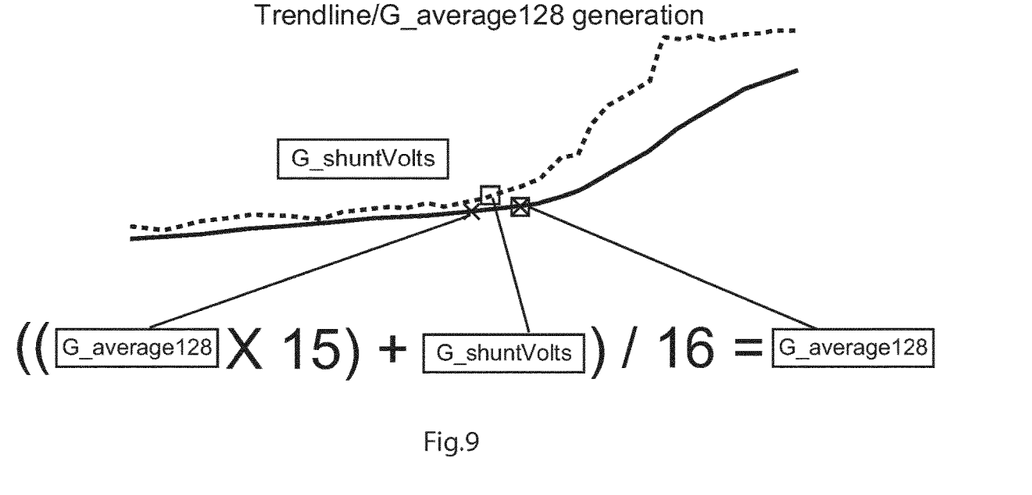
FIGS. 9 and 10 are plots showing operation of the processor in one example, in which the AP drive current drawn at each of three drive frequencies is recorded every 8 ms and a running average maintained in order to calculate a numerical output.

Referring to FIG. 9 for the steps 201 and 202 the controller records the drive current (as represented by shunt voltage) over an extended period, for the three frequencies by storing the data in a number of software buffers. It first determines the trend of the current draw for each frequency.

Every 8 ms the current drawn at each frequency is recorded and added to the previous average (using the formula shown below). The intention of this is to create a running baseline from which any sudden changes can be identified.

The baseline formula is calculated as:

$$((G\_Average128 \times 15) + G\_shuntVolts)/16 = G\_average128$$

where:
G_Average128 is the average value over the last 16 samples taken, based on the 128 kHz drive frequency, and
G_shuntVolts is the current detected drive current as represented by shunt voltage.

Figure 10:
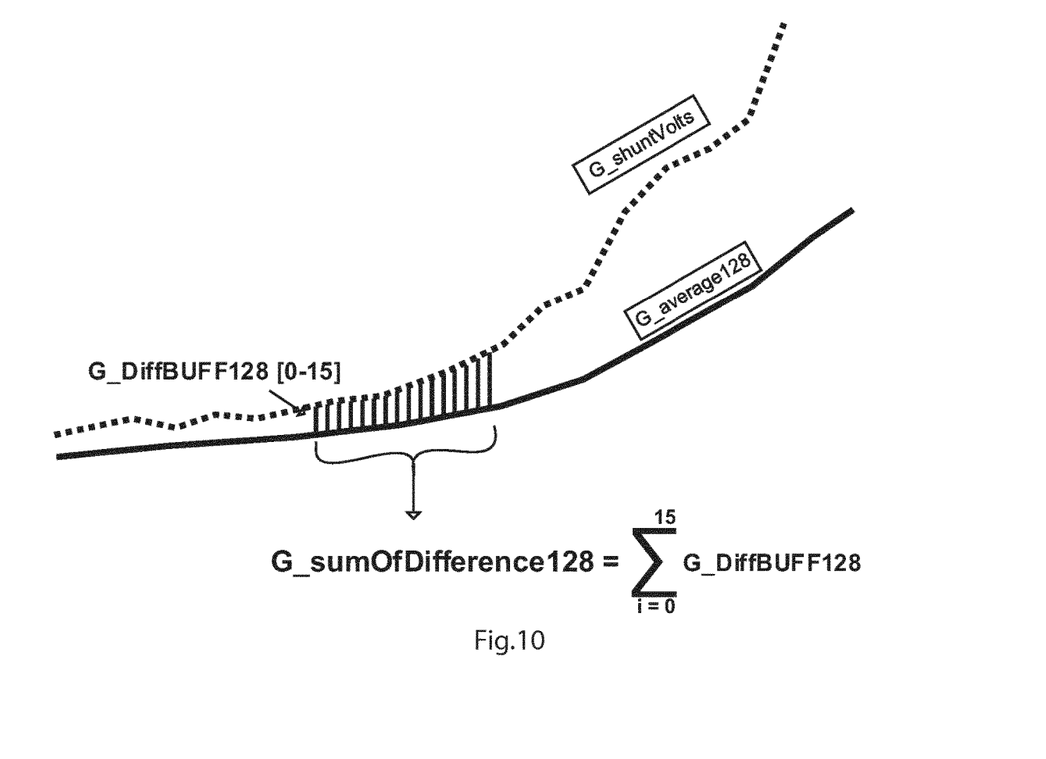
Figure 11:
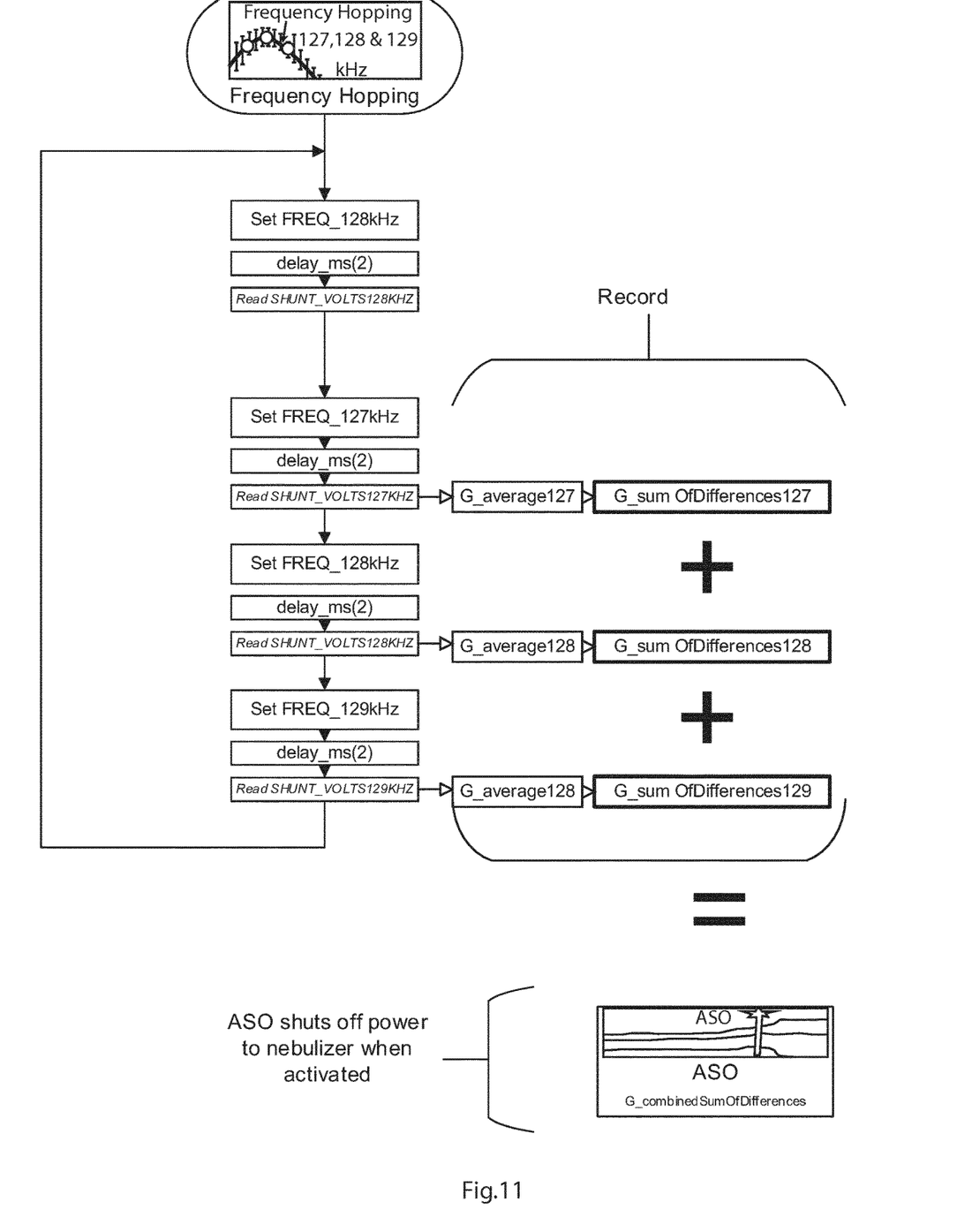
FIG. 11 is a flow diagram illustrating AP transition detection with the processor operations of FIGS. 9 and 10.

As shown in FIG. 10 a differential FIFO buffer is then used to record the difference from the baseline for a total of 16 readings (8 mS×16=128 mS). Every frequency (127 kHz, 128 kHz & 129 kHz) will have an individual buffer containing the previous 16 differential readings. For each frequency the difference buffer is totalled (G_sumOfDifference127/8/9). This is illustrated in FIG. 11.

The controller continues to deliver AP drive power while the following condition is met:

$$while(G\_combinedSumOfDifferences < ASO\_MAX\_DIFFERENTIAL)$$

Every 8 ms the combinedSumOfDifferences is compared to the predetermined maximum numerical output value (ASO_MAX_DIFFERENTIAL=3000).

If this maximum value is exceeded, an alert is triggered and power is immediately reduced or removed from the drive stage. The setting to decide on whether power is completely removed immediately or reduced progressively depends on the nature of the therapy. If the medication is small in volume then the controller may operate to a setting of gradual reduction. Otherwise, the controller setting will cause immediate removal of power upon detection of start of transition to dry.

It will be appreciated that the invention in a very effective manner avoids risk of the AP becoming dry, providing an optimum performance for protecting the AP while ensuring that there is optimum delivery of medication. It prevents significant physical plate displacement when a device changes from wet state to the dry state. For example, at 128 kHz operating frequency the displacement can change from 2 μm when wet to 4 μm or higher when dry.

Avoidance of this sudden change in displacement prevents plate deformation and damage.

The invention is not limited to the embodiments hereinbefore described which may be varied in detail. For example the residual liquid check step 204 may be performed by continuing with the cyclic drive and monitoring of the numerical output. If so, there may be more than one threshold level, such as a low level to provide the initial indication of potential transition (left peak of FIG. 7), one or more intermediate threshold levels which will provide an indication of whether the rise is noise or due to transition, and the top level which triggers immediate shut-down. If there is a scan performed for step 204 then the number of measuring points may differ from 5, and is preferably in the range of 2 to 20 and more preferably in the range of 3 to 10. It is envisaged that the residual volume check may be performed with use of additional sensing such as by image processing of a feed from a camera, or by sensing of another type such as optical LED sensing. The electrical characteristic which is monitored may be power consumed by the aerosol generator or a parameter such as drive current or voltage of phase.

The invention claimed is:

1. An aerosol delivery system comprising:
an aerosol generator comprising a vibrating aperture plate and an actuator, wherein the aperture plate has a plurality of apertures extending between a first surface which is adapted to receive a liquid to be aerosolised and a second surface at which an aerosol is generated, and
a controller for controlling operation of the aerosol generator,
wherein the controller is configured to perform in real time a method comprising the steps of:
monitoring at least one electrical characteristic of the aerosol generator as it is driven at a first power for vibration of the aperture plate;
detecting a change in the electrical characteristic in response to a transition from a wet state to a dry state of the aperture plate as it is driven at the first power; and
automatically modifying, during said transition, operation of the aerosol generator in response to said detected change, said modification including partially reducing power applied to the aerosol generator to a reduced power level, and
wherein the controller is configured to continue to monitor said change during the transition after the reduction in power to the reduced power level, including monitoring the aperture plate for presence of residual liquid on the aperture plate first surface; and wherein the controller is configured to activate the power at an incremental power level above the reduced power level but lower than the first power in response to detection of residual liquid on the aperture plate first surface during the transition.

2. The aerosol delivery system as claimed in claim 1, wherein the controller is configured to shut off power applied to the aerosol generator when the transition is about to complete.

3. The aerosol delivery system as claimed in claim 1, wherein the controller is configured to perform at least one of:
indicating a confirmation that the remaining liquid has been aerosolized;
shutting off power to the aerosol generator immediately after power-up if the aperture plate is in a dry state;
monitoring the electrical characteristic at an operating frequency and at one or more additional frequencies adjacent to the operating frequency; and
driving the aperture plate at said frequencies in cycles, wherein at least one additional frequency is within 5 kHz of the operating frequency.

4. The aerosol delivery system as claimed in claim 1, wherein the controller is configured to monitor the electrical characteristic at an operating frequency and at one or more additional frequencies adjacent to the operating frequency, and to monitor the electrical characteristic at a first frequency less than 5 kHz below the operating frequency and at a second frequency less than 5 kHz above the operating frequency to determine if a change has occurred, and wherein the duration of at least some of the monitoring steps at each frequency is in the range of 1 ms to 4 ms.

5. The aerosol delivery system as claimed in claim 1, wherein the controller is configured to monitor signals representing the electrical characteristic at each of a plurality of drive frequencies and maintains data representing trends in each signal and/or in a combination of the signals, and to identify a start of a transition if a calculated value representing deviation from said trend or trends rises above a threshold.

6. The aerosol delivery system as claimed in claim 1, wherein the controller is configured to monitor signals representing the electrical characteristic at each of a plurality of drive frequencies and maintains data representing trends in each signal and/or in a combination of the signals, and to identify a start of a transition if a calculated value representing deviation from said trend or trends rises above a threshold; and wherein the controller is configured to:
  for each drive frequency, maintain an average value for the electrical characteristic and detect a difference between a current value and said average, and
  combine said differences for all drive frequencies to provide said calculated value.

7. The aerosol delivery system as claimed in claim 1, wherein the controller is configured to monitor signals representing the electrical characteristic at each of a plurality of drive frequencies and maintains data representing trends in each signal and/or in a combination of the signals, and to identify a start of a transition if a calculated value representing deviation from said trend or trends rises above a threshold; and wherein the controller is configured to continue to monitor said change in electrical characteristic during the transition, including monitoring the aperture plate for presence of residual liquid on the aperture plate first surface, and wherein said continuation of monitoring confirms said identification of a start of a transition; and wherein the controller is configured to, if said calculated value rises above said threshold, confirm said identification by carrying out a scan by measuring an electrical characteristic at a plurality of measuring points each with a different drive frequency and determining if there is a residual volume according to said scan; and wherein said scan includes a number of measuring points in the range of 2 to 20; and wherein the controller is configured to perform the scan at a reduced applied power to the aerosol generator.

8. The aerosol delivery system as claimed in claim 1, wherein the controller is configured to monitor signals representing the electrical characteristic at each of a plurality of drive frequencies and maintains data representing trends in each signal and/or in a combination of the signals, and to identify a start of a transition if a calculated value representing deviation from said trend or trends rises above a threshold; and wherein the controller is configured to continue to monitor said change in electrical characteristic during the transition, including monitoring the aperture plate for presence of residual liquid on the aperture plate first surface, and wherein said continuation of monitoring confirms said identification of a start of a transition; and wherein the controller is configured to, if said calculated value rises above said threshold, confirm said identification by carrying out a scan by measuring an electrical characteristic at a plurality of measuring points each with a different drive frequency and determining if there is a residual volume according to said scan; and wherein the controller is configured to return to a driving mode after the scan and then automatically perform another scan within a pre-set time period.

9. The aerosol delivery system as claimed in claim 1, wherein the controller is configured to monitor signals representing the electrical characteristic at each of a plurality of drive frequencies and maintains data representing trends in each signal and/or in a combination of the signals, and to identify a start of a transition if a calculated value representing deviation from said trend or trends rises above a threshold wherein the controller is configured to store a high threshold value for the calculated value, and to immediately shut off power to the aerosol generator if the calculated value exceeds said high threshold.

10. A method of operation of an aerosol delivery system comprising:
  an aerosol generator comprising a vibrating aperture plate and an actuator, wherein the aperture plate has a plurality of apertures extending between a first surface which is adapted to receive a liquid to be aerosolised and a second surface at which an aerosol is generated, and
  a controller for controlling operation of the aerosol generator,
  the method being performed in real time by said controller and comprising steps of:
    monitoring at least one electrical characteristic of the aerosol generator as it is driven at an operating power for vibration of the aperture plate;
    detecting a change in the electrical characteristic in response to a transition from a wet state to a dry state of the aperture plate as it is driven at the operating power; and
    automatically modifying, during said transition, operation of the aerosol generator in response to said detected change, said modification including partially reducing power applied to the aerosol generator, and
    wherein the method comprises continuing to monitor the change in the electrical characteristic during the transition after the reduction in power to the reduced power level, including monitoring the aperture plate for presence of residual liquid on the aperture plate first surface; and wherein the method comprises activating the power at a series of incremental power levels lower than the operating power in response to detection of residual liquid on the aperture plate first surface during the transition, the power being activated at each of the incremental power levels after the reduction in power to the reduced power level; and
    shutting off power to the aerosol generator immediately after power-up if the aperture plate is in a dry state.

11. The method as claimed in claim 10, wherein the method comprises shutting off power applied to the aerosol generator when the transition is about to complete.

12. The method as claimed in claim 10, comprising monitoring the electrical characteristic at an operating frequency and at one or more additional frequencies adjacent to the operating frequency, the aperture plate being driven at said frequencies in cycles, wherein at least one additional frequency is within 5 kHz of the operating frequency.

13. The method as claimed in claim 10, comprising monitoring the electrical characteristic at an operating frequency and at one or more additional frequencies adjacent to the operating frequency, the aperture plate being driven at said frequencies in cycles, wherein at least one additional frequency is within 5 kHz of the operating frequency; and monitoring the electrical characteristic at a first frequency less than 5 kHz below the operating frequency and at a second frequency less than 5 kHz above the operating frequency to determine if a change has occurred; and wherein the duration of at least some of the monitoring steps at each frequency is in the range of 1 ms to 4 ms.

14. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold.

15. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold; and wherein the calculated value is based on trends in a combination of the signals.

16. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold; and wherein the calculated value is based on trends in a combination of the signals; and wherein the calculated value represents the sum of changes of the electrical characteristic at all of the drive frequencies.

17. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold; and wherein the calculated value is based on trends in a combination of the signals; and wherein the calculated value represents the sum of changes of the electrical characteristic at all of the drive frequencies; and wherein the controller:
for each drive frequency, maintains an average value for the electrical characteristic and detects a difference between a current value and said average, and
combines said differences for all drive frequencies to provide said calculated value.

18. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold; and wherein the calculated value is based on trends in a combination of the signals; and wherein the calculated value represents the sum of changes of the electrical characteristic at all of the drive frequencies wherein the method comprises continuing to monitor said change in electrical characteristic during the transition, including monitoring the aperture plate for presence of residual liquid on the aperture plate first surface, and wherein said continuation of monitoring confirms said identification of a start of a transition.

19. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold; and wherein the calculated value is based on trends in a combination of the signals; and wherein the calculated value represents the sum of changes of the electrical characteristic at all of the drive frequencies; and wherein, if said calculated value rises above said threshold, the controller confirms said identification by carrying out a scan by measuring an electrical characteristic at a plurality of measuring points each with a different scan frequency and determining if there is a residual volume according to said scan.

20. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold; and wherein the calculated value is based on trends in a combination of the signals; and wherein the calculated value represents the sum of changes of the electrical characteristic at all of the drive frequencies; and wherein, if said calculated value rises above said threshold, the controller confirms said identification by carrying out a scan by measuring an electrical characteristic at a plurality of measuring points each with a different scan frequency and determining if there is a residual volume according to said scan wherein said scan includes a number of measuring points in the range of 2 to 20.

21. The method as claimed in claim 10, wherein the controller monitors signals representing the electrical characteristic at each of a plurality of drive frequencies and maintains data representing trends in each signal and/or in a combination of the signals, and identifies a start of a transition if a calculated value representing deviation from said trend or trends rises above a threshold wherein the controller stores a high threshold value for the calculated value, and immediately shuts off power to the aerosol generator if the calculated value exceeds said high threshold.

* * * * *